(12) United States Patent
Silcott et al.

(10) Patent No.: US 6,885,440 B2
(45) Date of Patent: Apr. 26, 2005

(54) SYSTEM AND METHOD FOR DETECTING AND CLASSIFYING BIOLOGICAL PARTICLES

(75) Inventors: David B. Silcott, Reisterstown, MD (US); Greg A. Tilley, Monkton, MD (US); Brian R. Whitman, Towson, MD (US); Steven J. Pratt, Baltimore, MD (US)

(73) Assignee: S31, LLC, Owings Mills, MD (US)

( * ) Notice: Subject to any disclaimer, the term of this patent is extended or adjusted under 35 U.S.C. 154(b) by 173 days.

(21) Appl. No.: 10/289,266

(22) Filed: Nov. 7, 2002

(65) Prior Publication Data
US 2003/0098422 A1 May 29, 2003

Related U.S. Application Data
(60) Provisional application No. 60/331,048, filed on Nov. 7, 2001, and provisional application No. 60/383,776, filed on May 30, 2002.

(51) Int. Cl.[7] .............................. G01N 21/00; G21G 5/00
(52) U.S. Cl. ...................... 356/73; 356/343; 356/344; 250/492.1; 436/172
(58) Field of Search .......................... 356/73, 343, 344, 356/438, 439, 440, 442, 71; 250/492.1; 436/172

(56) References Cited

U.S. PATENT DOCUMENTS

| | | | |
|---|---|---|---|
| 3,566,114 A | 2/1971 | Brewer | |
| 4,173,415 A | * 11/1979 | Wyatt | .......................... 356/336 |
| 4,548,500 A | * 10/1985 | Wyatt et al. | ................. 356/336 |
| 4,651,010 A | 3/1987 | Javan | |
| 4,679,939 A | 7/1987 | Curry et al. | |
| 4,710,025 A | * 12/1987 | Wyatt et al. | ................. 356/343 |
| 5,474,910 A | 12/1995 | Alfano | |
| 3,470,373 A | 9/1996 | Brewer et al. | |
| 5,619,324 A | 4/1997 | Harvill et al. | |
| 5,701,012 A | 12/1997 | Ho | |
| 5,866,430 A | * 2/1999 | Grow | .......................... 436/172 |
| 5,895,922 A | * 4/1999 | Ho | ........................... 250/492.1 |
| 5,999,250 A | 12/1999 | Hairston et al. | |
| 6,040,191 A | * 3/2000 | Grow | .......................... 436/172 |
| 6,040,574 A | 3/2000 | Jayne et al. | |
| 6,118,531 A | 9/2000 | Hertel et al. | |
| 6,122,042 A | * 9/2000 | Wunderman et al. | ......... 356/73 |
| 6,194,731 B1 | 2/2001 | Jeys et al. | |
| 6,482,652 B2 | * 11/2002 | Furlong et al. | ............... 436/63 |

OTHER PUBLICATIONS

"A Fluorescence Particle Detector for Real Time Quantification of Viable Organisms in Air," Greg Luoma et al., presented at SPIE International Symposium on Environmental and Industrial Sensing, Boston, MA, Oct. 28–Nov. 2, 2001, published in Proceedings.

(Continued)

*Primary Examiner*—Gregory J. Toatley, Jr.
*Assistant Examiner*—Roy M. Punnoose
(74) *Attorney, Agent, or Firm*—Kilpatrick Stockton, LLP

(57) ABSTRACT

A continuous wave laser excites a biological particle. Detection channels are created to detect light scattered by the biological particle, and to detect any auto-fluorescence emitted by the biological particle. Additional channels can also detect light emitted by auto-fluorescence of the biological particle when simultaneously excited by light at harmonics of the laser's fundamental wavelength. The biological particle is identified using Mie scattering and auto-fluorescence. Ratio-metric calculations generated by calculating ratios of detected peak heights or integrated pulse values in the channels provides additional information for identifying and classifying the biological particle. A warning or alert can be provided if the identified biological particle is a particle of interest.

20 Claims, 13 Drawing Sheets

OTHER PUBLICATIONS

Differences In Detected Fluorescence Among Several Bacterial Species Measured with a Direct–Reading Particle Sizer and Fluorescence Detector, Lisa M. Brosseau et al., Aerosol Science and Technology 32:545–558 (2000).

Detection of Bioaerosols Using Multiwavelength UV Fluorescence Spectroscopy, Y.S. Cheng et al., Aerosol Science and Technology 30:186–201 (1999).

Real–time Measurement of Fluorescence Spectra from Single Airborne Biological Particles, Ronald G. Pinnick et al., Field Analytical Chemistry and Technology, 3, 221–239 (1999).

Laser–Induced Autofluorescence for Medical Diagnosis, K. Koenig et al., Journal of Fluorescence, vol. 4, No. 1, 1994.

Fluorescence and Time–Resolved Delayed Luminescense of Porphyrins in Organic Solvents and Polymer Matrices, D. Wrobel et al., Journal of Fluorescence, vol. 8, No. 3, 1998.

* cited by examiner

SYSTEM AND METHOD FOR DETECTING AND CLASSIFYING BIOLOGICAL PARTICLES

This application claims the benefit of U.S. Provisional Application No. 60/331,048, filed Nov. 7, 2001, and U.S. Provisional Application No. 60/383,776, filed May 30, 2002, both of which are herein incorporated by reference in their entireties.

BACKGROUND

1. Field of the Invention

The present invention relates generally to instruments and methods for analyzing airborne biological particles. More particularly, the present invention relates to instruments and methods for classifying and identifying airborne biological particles in real-time based on both their size and laser-induced auto-fluorescence of their biological components.

2. Background of the Invention

Numerous airborne pathogens and allergens can be found in or introduced into an environment. These airborne particles can be naturally occurring or artificially produced. Some of these airborne particles can be dangerous, and even life threatening. For example, such airborne particles can include biological agents such as those that can be used for military purposes or as weapons of terror by terrorist organizations. To avoid widespread illness or death, there is a need for real-time detection of airborne biological particles. Early warning provided by real-time detection of such airborne biological particulates minimizes human exposure to such harmful airborne pathogens, allergens, and biological warfare agents.

For military and counter-terrorism applications, rapid detection of a biological aerosol attack is often essential for effective treatment. Table 1, for example, shows exemplary exposure levels required (in numbers of biological warfare agent particles) to produce an infectious response by inhalation if treatment is not provided in a timely manner.

TABLE 1

Numbers of biological particle likely to be lethal if inhaled and not timely treated

| Biological Warfare Agent | Number of Particles Required to Produce a Lethal Response by Inhalation |
|---|---|
| Bacillus anthracis spores (Anthrax) | 8,000–10,000 |
| Yersinia pestis (Bubonic Plague) | 10–100 |
| Franciscella tularensis (Tularemia) | 10–100 |
| Smallpox | 1–10 |

Due to the low number of biological particles required for various agents to produce an infectious response, biological aerosol detection systems should be able to detect low levels of biological warfare agent aerosol concentrations. Aerosol attacks delivering, as low as, a biological particle per liter of air can still provide a life threatening level of biological warfare agents. Consequently (referring to Table 1), a major challenge for real-time detection systems is that they be capable of detecting trace levels of airborne biological agents.

Other applications also require the real-time detection of individual airborne biological particles. For example, airborne detection of organisms in pharmaceutical and biotechnology production facilities can be used to provide verification and validation that there has been no contamination to drugs or other biological compounds produced in these environments. Airborne detection of biological particles can also be used to monitor organism levels in hospitals and other critical care facilities to prevent post-operative infections and the spreading of disease in such facilities. Monitoring of airborne biological particulates at animal processing and sewage treatment facilities can be used to ensure industrial hygiene. Detection of commonly encountered pathogens in a building's HVAC system can be used for purposes of indoor air quality monitoring. Detection of pollens and other biological particulates in outdoor environments can also be used in meteorological and aerosol research applications. Thus, it can be seen that real-time detection of biological particles is required for a variety of applications, including those described above.

One method for characterizing individual airborne biological particles in real-time is measuring laser-induced auto-fluorescence of biological particles. The majority, if not all, biological particles in nature have one or more endogenous fluorophores associated with it. Such endogenous fluorophores comprise biological or biochemical components that absorb light at a particular frequency and emit fluorescence at another particular frequency. The emitted fluorescence frequency is dependent on the absorption frequency. The biological or biochemical components in different endogenous fluorophores are excited by light having different frequencies and fluoresce at different frequencies. These different fluorescence frequencies can be used as a signature to characterize and identify each biological or biochemical component in a biological particle. That is, because different biological particles are comprised of different combinations of biological or biochemical components, as well as, different concentrations of endogenous fluorophores relative to the biological particle's size, detection and analysis of fluorescing and Mie scattering characteristics can be used to detect and classify the biological particles.

These endogenous fluorophores include flavins, the coenzymes NADH and NADPH, the amino acids tryptophan and tyrosine, porphyrins. Table 2 provides a list of common endogenous fluorophores, and their corresponding absorption and fluorescence emission wavelengths.

TABLE 2

Endogenous Fluorophore Absorption and Fluorescence Maxima

| Fluorophore | Absorption (nm) | Fluorescence (nm) |
|---|---|---|
| Tryptophan | 220,280,288 | 320–350 |
| Thyrosin | 220,275 | 305 |
| Collagen | 300–340 | 420–460 |
| Elastin | 300–340 | 420–460 |
| NADH | 260,340 | 470 |
| NADPH | 260,340 | 470 |
| Flavins | 260,370,450 | 530 |
| Zn-coproporphyrin | 411,539,575 | 580 |
| Zn-protoporphyrin | 421,548,585 | 592 |
| Uroporphyrin | 404,501,533,568,622 | 624 |
| Coproporphyrin | 398,497,531,565,620 | 622 |
| Protoporphyrin | 406,505,540,575,630 | 633 |
| Chlorophyll a | 425,670 | 685 |
| Chlorophyll b | 455,642 | 660 |

Auto-fluorescence of individual biological particles is typically induced by exciting the biological particles with a laser. Laser-induced auto-fluorescence uses a laser to illuminate a biological particle with light having a wavelength that causes endogenous fluorophores in the biological particle to fluoresce.

To more accurately classify biological particles, their size can also be considered. Certain known biological particles have certain sizes. Particles of different sizes can contain similar endogenous fluorophores. Consequently, combining size and auto-fluorescence information can provide more accurate detection and characterization of particular biological agents.

Conventional techniques for detecting individual airborne biological particles use a two laser system. A first laser is used to determine particle size. The second laser is a UV laser that is used to provide an auto-fluorescence measurement. Particle size is determined by time of flight or Mie scattering (also called elastic scattering) measurements. The second laser is pulsed based on a triggering signal generated as a function of the particle's size. Such a system, for example, is disclosed in U.S. Pat. No. 5,999,250 to Hairston et al. ("Hairston"). Hairston discloses a two laser system for determining particle size and detecting fluorescence wherein a first laser (in the visible region) is used to determine a particle's size by a time-of-flight measurement. The particle size is then used to determine a delay (based on particle size) after which to trigger the second laser (in the UV region) as the particle passes through the second laser's beam.

U.S. Pat. No. 5,895,922 to Ho also discloses a two-laser system for determining particle size and detecting fluorescence wherein a first laser (in the visible region) is used to determine a particle's size by a time-of-flight measurement. In one embodiment of the system disclosed in Ho, the UV laser is triggered on the basis of the particle's location. In another embodiment of the system disclosed in Ho, the UV laser is continuous. In this embodiment, a window generator opens a collection window (of approximately 1 us) during which fluorescence signals from a PMT are collected.

One problem potentially encountered with such triggered systems is an increased likelihood of not detecting a certain percentage of biological particles at elevated aerosol concentrations due to triggering limitations. This is a significant issue when detecting airborne biological particles due to the fact that the percentage of biological particles in most environments is less than 0.1% of the total aerosol content.

SUMMARY OF THE INVENTION

The present invention uses a single excitation source applied to a stream of particulates to both determine the size of the particles in the stream and to classify the particles. The stream of particles can be, for example, in an aerosol containing the particles captured from an environment surrounding a capture device. Preferably, the excitation source is a single wavelength laser diode. Detection optics detect light emitted at a plurality of frequencies (or wavelengths). Light emitted at the frequency of the illuminating laser beam is used to size the particle using Mie scattering techniques. Light emitted at fluorescence frequencies and the size of the particle is used to biologically classify the particles.

Biological classification is performed by exciting the particles at one or more absorption frequencies of endogenous fluorophores that are expected to be present in the biological particles of interest. In one embodiment of the present invention, the laser diode is chosen such that its wavelength can be divided to produce harmonics that cause desired effects to enable biological classification of the particles.

When a biological particle is illuminated with a laser diode having a wavelength that can be absorbed by the particle's endogenous fluorophores, the absorbing endogenous fluorophores fluoresce. The present invention detects the light emitted from the fluorescing biological particles. Preferably, this is done by placing short or long bandpass filters in front of an array of photo-multiplier tubes (PMT) to admit only selected frequencies of light to be received by each PMT in the array. The use of filters allows the present invention to detect multiple fluorescing frequencies in separate channels.

After the signals are detected by the PMT, the signals from the PMT are fed to a high-speed circuit that performs either pulse height analysis for each individual channel or the signal's voltage for each channel is integrated in an incremental manner as the aerosol particle traverses the laser beam. When performing pulse height analysis the peak voltage for each channel is measured during each aerosol particulate event that traverses the laser beam. When performing pulse integration, the analog pulse generated by an aerosol particle traversing the laser beam is measured in an incremental manner when a predefined threshold voltage level is exceeded. While the channel's voltage remains higher than the threshold voltage the voltage value for each increment is added to the voltage values obtained from previous increments. This incremental recording of the voltage is performed until the signal falls below the threshold or until a predefined period has elapsed.

By measuring those values, obtained either by pulse height analysis or pulse integration, and then comparing those values using ratio-metric calculations further species identification is provided. Ratio-metric calculations include, for example, determining the height of pulses detected in different channels to one another or by determining the integrated values obtained by pulse integration in different channels to one another. The degree of fluorescence of each of these biochemical components within a biological particle as they relate to the particle size as well as to each other provides a means for a greater identification. For example, the signal generated in the flavins channel can be compared with the signal generated in the size scattering channel to perform a ratio-metric of calculation that provides additional information that can be used to identify the biological particle of interest.

The circuit can analyze the detected signals in a real-time manner. The analog signals are first converted into digital signals using a high-speed analog-to-digital converter. The digital signals fed into a field programmable gate array, which performs the peak detection followed by the ratio-metric calculations of each individual aerosol event. For either pulse height analysis mode or pulse integration mode, the comparisons of the light detected in different channels are compared with a library inside field-programmable gate array to classify the biological agents in the aerosol. The library comprises the channel ratios of commonly-encountered aerosols in an environment. In addition, the library comprises aerosols that have already been detected in this environment. Thus, the library comprises known signatures for known biological components. The library can be configured for biological warfare agents by comparing the signatures collected for these agents with those expected for commonly encountered biological aerosols for example mold spores, plant pollens, other bacteria and bacterial spores that are commonly encountered in a building environment as well as an outdoor environment. Warnings or alerts can be provided if the comparison indicates that a biological event of interest has been detected.

DETAILED DESCRIPTION OF THE INVENTION

The present invention provides real-time detection of the presence of biological particles that are sampled from the air in a real-time manner. Preferably, the detection process of the present invention comprises two primary components. The first component includes collecting the aerosol containing airborne particles, introducing the collected aerosol into a laser's viewing region and collecting the amount of generated light. The second component of the detection process includes analysis of the signals collected from a sensor.

The sensor comprises four primary components. An aerosol inlet probe is used to analytically introduce the aerosol to a laser's viewing volume. An aerosol outlet probe is preferably configured to remove the aerosol that exits from the laser's view volume to minimize fouling of the optic region of the sensor itself. An illumination source that comprises either a continuous wave laser or a modulated laser with a repetition frequency that exceeds 50 MHz. The sensor includes means for collecting the light when the laser illuminates a particle.

The laser itself preferably generates a laser beam that is either a line laser beam or a collimated beam. Preferably, scattered and/or fluorescing light is collected using wide angle light collection techniques. As described in more detail below, this can be accomplished using either aspheric condenser lenses or ellipsoidal reflectors. The collected light is then detected. For example, the scattered and/or fluorescing light can be detected by a photo-multiplier tube array.

Figure 1:
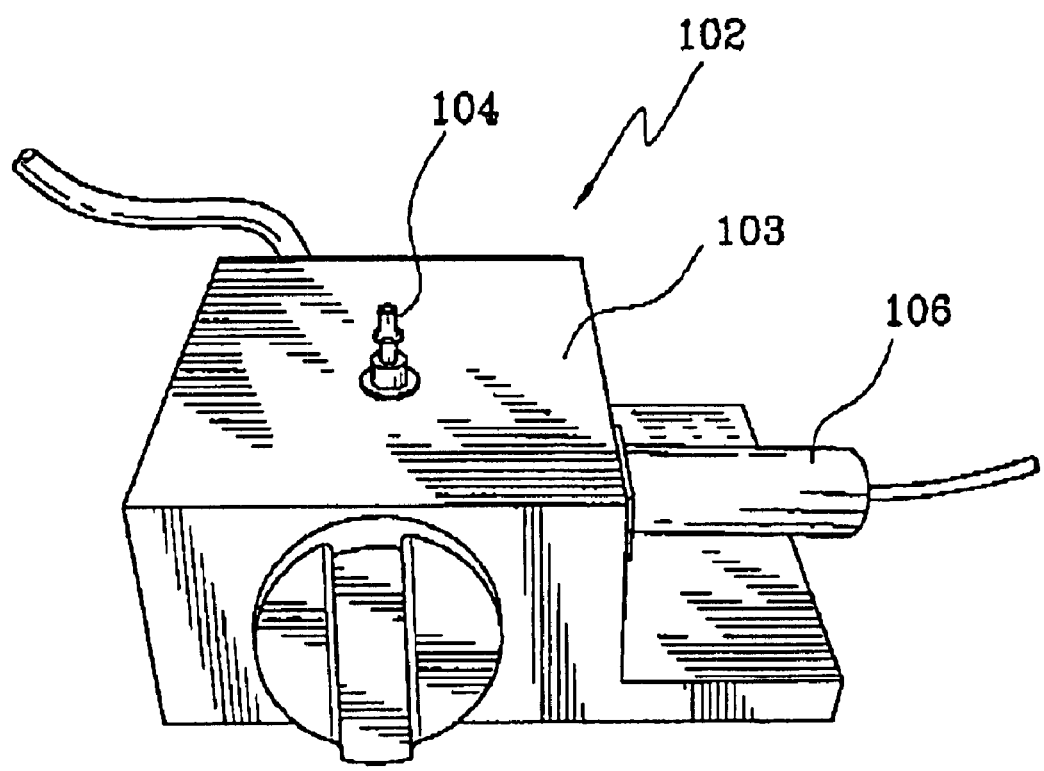
FIG. 1 is a schematic diagram illustrating an exemplary embodiment of a device for detecting airborne biological particles according to an embodiment of the present invention.

FIG. 1 is a schematic diagram illustrating an exemplary embodiment of an apparatus 102 for detecting airborne biological particles according to an embodiment of the present invention. Apparatus 102 includes a housing 103. Housing 103 includes an aerosol nozzle 104 in which air from an environment is injected for analysis. For example, the air can be from an environment surrounding apparatus 102 or air from another environment that is transported to aerosol nozzle 104. Housing 103 also includes a hole or other opening so that a laser 106 can be positioned in housing 103 so as to illuminate an aerosol injected into the laser through aerosol nozzle 103.

Figure 2:
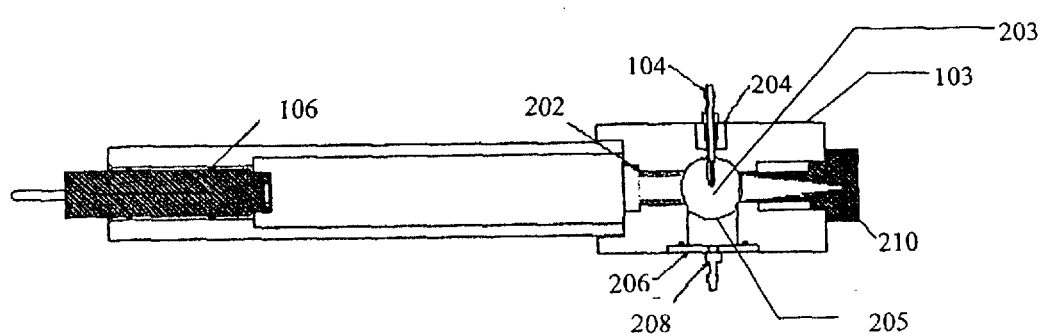
FIG. 2 is a schematic diagram illustrating a device for detecting airborne biological particles showing laser-aerosol orientation according to an embodiment of the present invention.

FIG. 2 is a schematic diagram illustrating a device for detecting airborne biological particles showing the orientation of the laser relative to the injected aerosol according to an embodiment of the present invention. Laser 106 generates a light beam that is introduced to view region (or chamber) 203 for detection by detection optics 205 through a light aperture 202. Detection optics 205 is preferably a configuration of optical lenses and mirrors as described in more detail below.

The light emitted by laser 106 illuminates an aerosol injected into view region 203 through aerosol nozzle 104. Aerosol nozzle 104 is affixed to housing 103 via a nozzle insert 204. The vacuum pump provides flow rates that draw the aerosol into view region 205 from the outside. The flow rate at which the vacuum pump draws aerosol into view region 205 can be varied from a few milliliters per second to approximately 9 liters per minute, depending on the application. A lens cover 206 provides access to detection optics 205 for installation and maintenance. A light stop 210 prevents light scatter that can interfere with the light detected by detection optics 205.

Figure 3:
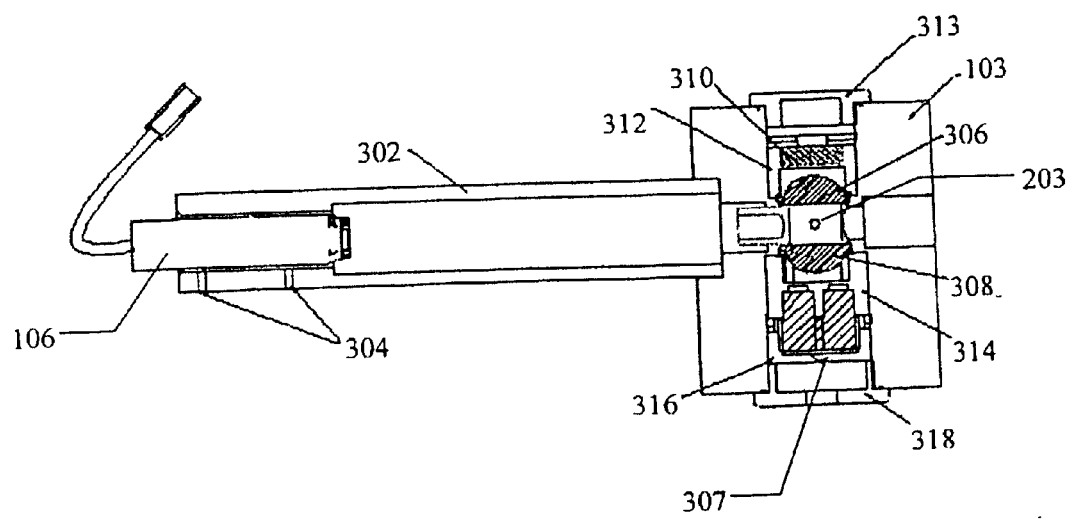
FIG. 3 is a schematic diagram illustrating a device for detecting biological particles showing laser-detection optics orientation according to an embodiment of the present invention.

FIG. 3 is a schematic diagram illustrating a device for detecting airborne biological particles showing the orientation of the laser with the detection optics according to an embodiment of the present invention. Laser 106 transmits its beam through a laser barrel 302. The light enters view region 203 where it is scattered and/or causes fluorescence. The position of the beam generated by laser 106 can be adjusted by laser adjustment screws 304. In the embodiment shown, light scatters or fluoresces directly to a collector assembly 307 through a collector lens 308 or indirectly through a lens 306 after reflection by a mirror 310.

In the embodiment illustrated in FIG. 3, lens 306 directs light going through it to a mirror 310. Mirror 310 is separated from lens 306 by a mirror spacer 312. A mirror cap 313 provides access to mirror 310 for installation and replacement.

Collector assembly 307 can be any quantitative light collector. For example, in the exemplary embodiment of the present invention illustrated in FIG. 3, collector assembly 307 is a photo-multiplier tube. Light the entering photo-multiplier tube 307 is collected and transmitted to analysis electronics (described below). Filters can be placed in front of photo-multiplier tube 307 so that only light of a particular wavelength is introduced to photo-multiplier tube 307. Photo-multiplier tube 307 is housed in a photo-multiplier tube housing 314 in a photo-multiplier tube retainer 316. Access to photo-multiplier tube 307 is gained via a photo-multiplier tube cap 318. Other embodiments of collector assembly 307 are described below.

Preferably, laser 106 is a continuous wave laser or a modulated laser with a repetition frequency of 50 MHz or greater. Use of such a laser avoids the disadvantages associated with lower frequency pulsed lasers based on triggering signals described above. Moreover, the error or delay that is inherent in triggering pulse-based systems is avoided by using such a laser. Thus, the present invention does not have the problem of under-sized sizes estimates, incorrect fluorescing or susceptibility to missing bioparticulate events.

Laser 106 comprises a laser diode. Numerous laser diodes are available that can provide a single wavelength excitation source for use in the present invention. For example, a laser diode that generates light having a wavelength of 405 nm can be used. As shown in Table 2, particles that absorb light in this region have maximum fluorescence emissions in the 530 nm and 580–720 nm regions. Thus, detection of the fluorescing wavelength of a particle illuminated with light at a frequency of 405 nm can be used to classify that particle biologically by detecting the presence of flavins, porphyrins and chlorophylls.

More flexibility is obtained by using an excitation source from which harmonics of the fundamental excitation wavelength can be generated. For example, excitation using and 808 nm laser diode allows for generation of second and third harmonics of 404 nm and 269 nm respectively. As shown in Table 2, this extends the range of fluorescence to emission bands in the 320–350 nm, 470–530 nm and 580–720 nm ranges permitting the detection of tryptophan, flavins, porphyrins and chlorophylls. Other ranges can be selected to provide the same or different fluorescence ranges. For example, excitation with a laser diode generating light at 830 nm provides a second harmonic at 415 nm and a third harmonic at 277 nm. This allows viewing of emissions in the 320–350 nm, 475–530 nm and 580–720 nm ranges permitting the detection of tryptophan, flavins, porphyrins and chlorophylls. Other useful laser diodes and their harmonics frequencies are a 1,064 nm laser diode that can provide first, second and third harmonic wavelengths of 532 nm, 354 nm and 266 nm to provide the ability to sense up to four to five endogenous floriferous classes permitting the detection of tryptophan, flavins, NADH/NADPH, porphyrins and chlorophylls. Two other fundamental frequencies that are particularly useful for generating required harmonics are 1,047 nm and 1,053 nm.

The harmonics can be created in several ways. For example, a well-known way of generating second, third and fourth harmonics of a fundamental wavelength of light is by passing a laser output through a non-linear optical material such as a nonlinear crystal or a glass fiber that has been doped with a nonlinear optical material. The resulting output will be composed of light at several harmonics.

Sizing of the particles is preferably performed using Mie (Rayleigh) scattering by illuminating the particle with a laser. For example, bacterial spore Anthrax exhibits a light scattering diameter of approximately 0.8 micron to 1.4 micron when illuminated with a laser.

After a particle is sized, a determination can be made as to whether the particle is a biological compound or not by detecting fluorescence in the expected emission bands. If there is no such emission, the particle is not biological. If there are such emissions, the type of biological compound can be determined by analyzing the particular fluorescent emissions and the particle size. For example, bacterial spores that contain the endogenous fluorophores flavins, NADH, NADPH, porphyrin family compounds and/or tryptophan can be illuminated by light having a different wavelengths to look for fluorescent emissions at wavelengths corresponding to each of these endogenous fluorophores. For example, illumination of a particle containing riboflavin will fluoresce at approximately 490–580 nm if illuminated by light in the 405 nm range.

Separate channels can be used to detect fluorescent emissions in multiple ranges at the same time. For example, a channel can be dedicated to detecting fluorescence in the 430–590 nm region again using appropriate filtering. Such a channel can detect, for example, flavins illuminated by light in the 405 nm region. Another channel could be devoted to detecting fluorescence in the 620–680 nm region. Such a channel could detect, for example, chlorophyll illuminated by light in the 405 nm region.

The outputs of the channels can also be used to perform ratio-metric calculations. In ratio-metric calculations, the peak outputs or integrated pulse outputs of each channel for a particular time frame are compared to one another to determine ratios. The ratios can be compared to a library of stored ratios expected for particular biological components in a particular environment. These comparisons, or ratios, can be used to assist in identifying or classifying biological particles.

FIG. 4 is schematic diagram providing a more detailed view of one embodiment of the detection optics of the present invention. The embodiment illustrated in FIG. 4 is similar to the embodiment of the detection optics illustrated in FIG. 3. Biological particles in an aerosol are injected into a detection apparatus through an aerosol nozzle 402 (for example, aerosol nozzle 104) through a view volume 404 and out of the detection apparatus through a aerosol outlet 406. As described above, as each particle passes through view volume 404, it is illuminated by a laser beam causing it to scatter the laser light and/or fluoresce. The laser beam is preferably oriented ninety (90) degrees to the collection optics show in FIG. 4.

The scattered or fluorescing light can pass through a condenser lens 408. Preferably, condenser lens 408 is an aspheric condenser lens that provides a collection angle of approximately 102 degrees. Collimated light exiting condenser lens 408 light impinges on an interference filter assemble 410. Interference filter assembly 410 is comprised of one or more interference filters. Each interference filter substantially allows light of only a particular frequency to pass through it to a detector 412. For example, in the embodiment of the present invention illustrated in FIG. 4, detector 412 is a photo-multiplier tube (PMT) assembly. PMT assembly 412 preferably includes a plurality of photo-multiplier tubes. The photo-multiplier tubes in detector 412 detect the amount of light passing through each filter. Detector 412 preferably comprises a detector corresponding to each filter in interference filter assembly 410. The filter(s) and corresponding detector(s) provide detection channels for the present invention, wherein there is a channel corresponding to each filter/detector pair.

Scattered or fluorescing light can also travel in a path away from detector 412. Light traveling away from detector 412 passes through a condenser lens 414. Preferably, condenser lens 414 is an aspheric condenser lens that provides a collection angle of approximately 102 degrees. Collimated light exiting condenser lens 414 reaches a mirror 416. Mirror 416 reflects the light back toward detector 412. The reflected light is focused by condenser lens 414 through view volume 404 so that it is passed by condenser lens 408 to interference filter assembly 410. Reflecting and focusing the light traveling away from detector 412 back to detector 412 helps to optimize the detection of any scattered or fluorescing light by detector 412.

Figure 4:
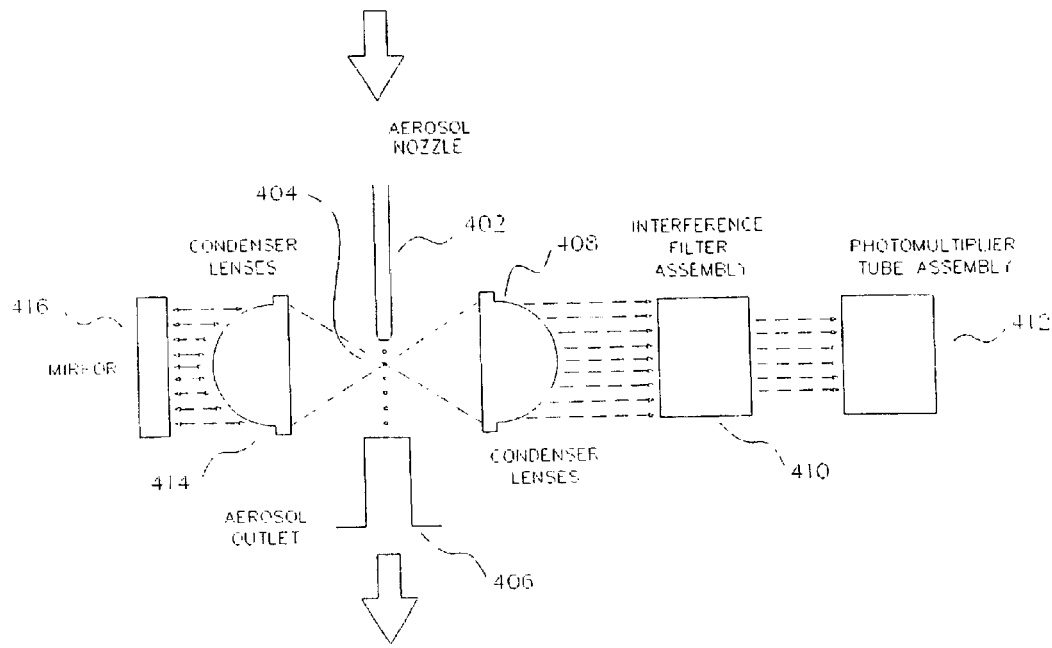
FIG. 4 is a schematic diagram providing a more detailed view of an embodiment of the detection optics of the present invention.
Figure 5:
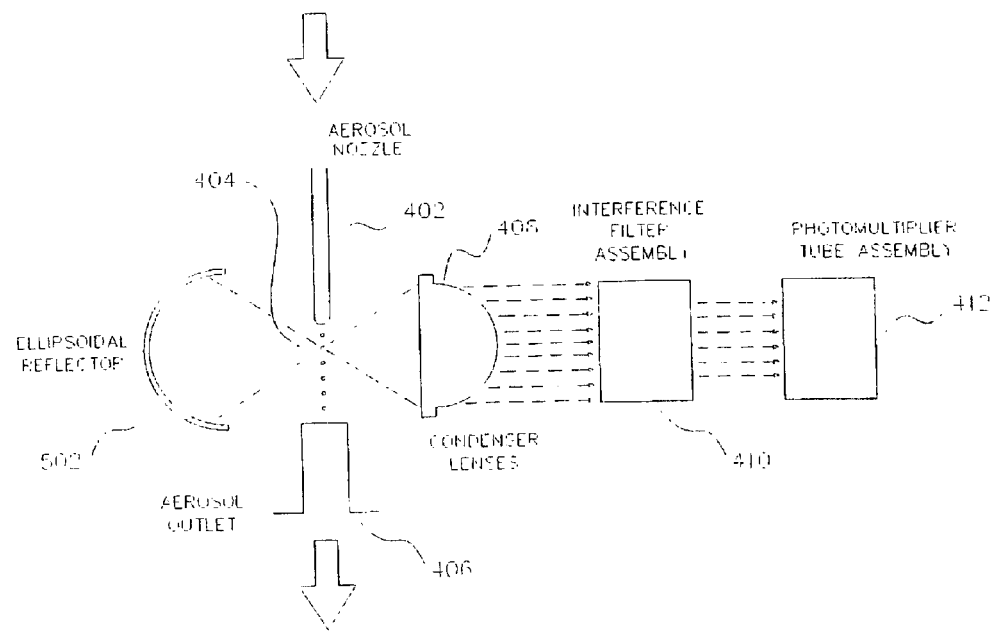
FIG. 5 is a schematic diagram illustrating another embodiment of the detection optics of the present invention.

FIG. 5 is a schematic diagram illustrating another embodiment of the detection optics of the present invention. An ellipsoidal reflector 502 is used to reflect light that travels away from detector 412 back to detector 412 rather than condenser lens 414 and mirror 416 as shown in FIG. 4.

Figure 6:
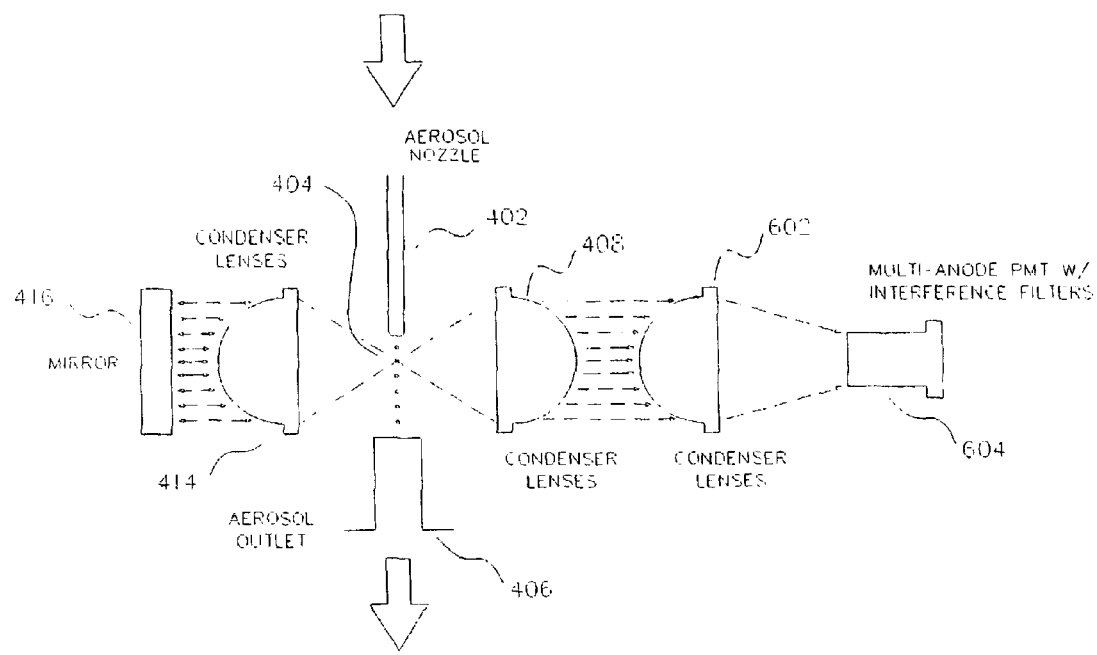
FIG. 6 is a schematic diagram illustrating another embodiment of the detection optics of the present invention.

FIG. 6 is a schematic diagram illustrating another embodiment of the detection optics of the present invention. A multi-anode PMT 604 comprises a plurality of interference filters physically affixed to a surface of multi-anode PMT 604. An exemplary multi-anode PMT for use in the embodiment of the present invention shown in FIG. 6 is multi-anode PMT model number H8352 available from Hamamatsu Corporation in Bridgewater, N.J. Using multi-anode PMT 604 allows for compact integration of the optical components to detect the light entering multi-anode PMT 604. More compact integration of the detection optics enables reduction of the size of the airborne particle detection device of the present invention.

In addition, use of a multi-anode PMT 604 allows further optimization of collecting scattered or fluorescing light. This is because using a physically separate interference filter assembly (as shown in FIGS. 4 and 5) is generally suboptimal due to dead regions in which the collection of light is not as efficient as with other parts of the filter surface. Use of a multi-anode PMT device largely avoids this inefficiency.

In addition to the use of multi-anode PMT 604, preferably, another condenser lens 602 is used to focus the scattered and/or fluorescing light onto the detectors of multi-anode PMT 604. Focusing the light in this manner helps to optimize the amount of light that impinges on each detector in multi-anode PMT 604. Condenser lens 602 can be any focusing element that can focus light from view volume 404 onto multi-anode PMT 604.

Figure 7:
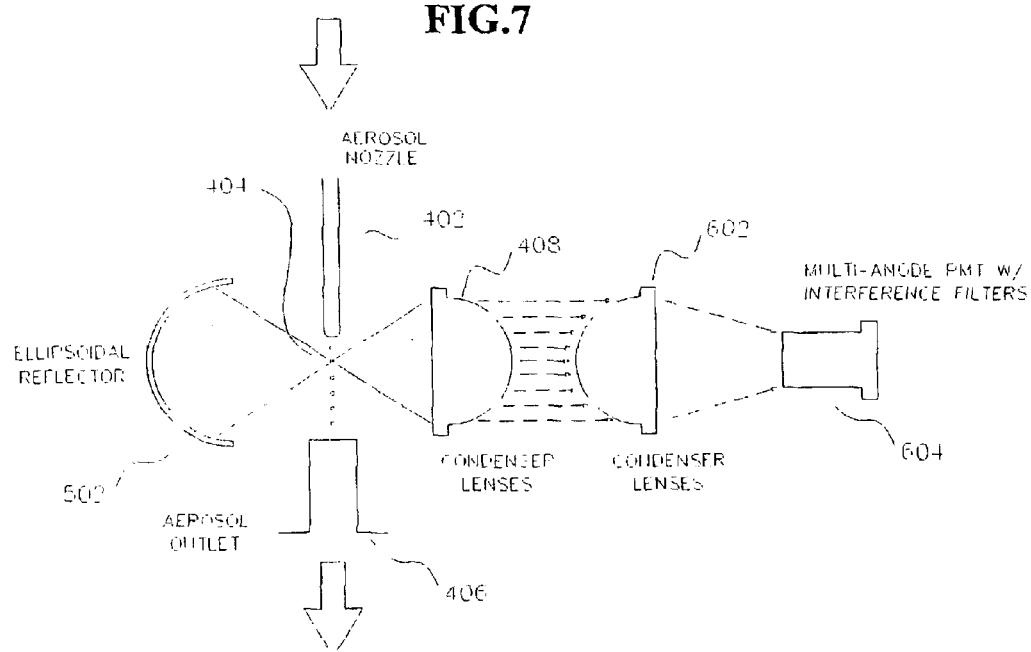
FIG. 7 is a schematic diagram illustrating another embodiment of the detection optics of the present invention.

FIG. 7 is schematic diagram illustrating another embodiment of the detection optics of the present invention. An ellipsoidal reflector 502 is used to reflect light that travels away from multi-anode PMT 604 back to multi-anode PMT 604 rather than condenser lens 414 and mirror 416 as shown in FIG. 6.

Figure 8:
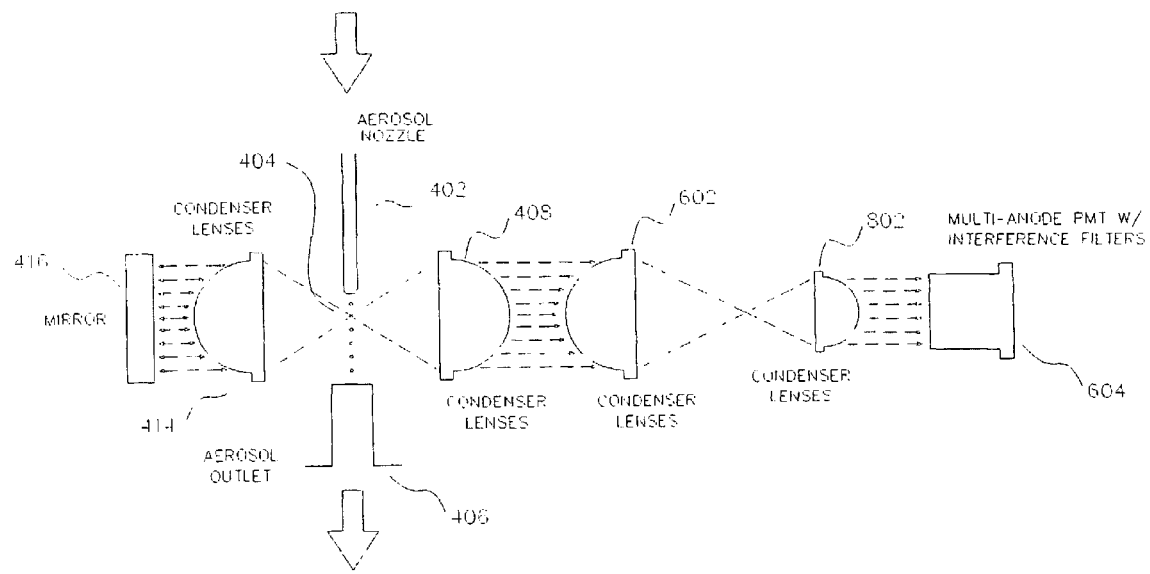
FIG. 8 is a schematic diagram illustrating another embodiment of the detection optics of the present invention.

FIG. 8 is a schematic diagram illustrating another embodiment of the detection optics of the present invention. In FIG. 8, a condenser lens 802 provides a collimated light output to multi-anode PMT 604. Collimating the light output by condenser lens 602 in this manner optimizes the light detected by the detectors in multi-anode PMT 604 by presenting a better light receiving angle to those detectors. Condenser lens 602 focuses light received from view volume 404 onto a condenser lens 802. Condenser lens 602 can be any focusing element that can focus light output from view volume 404 onto condenser lens 802. Condenser lens 802 collimates the light it receives from condenser lens 602 and outputs that the collimated light to multi-anode PMT 604.

Figure 9:
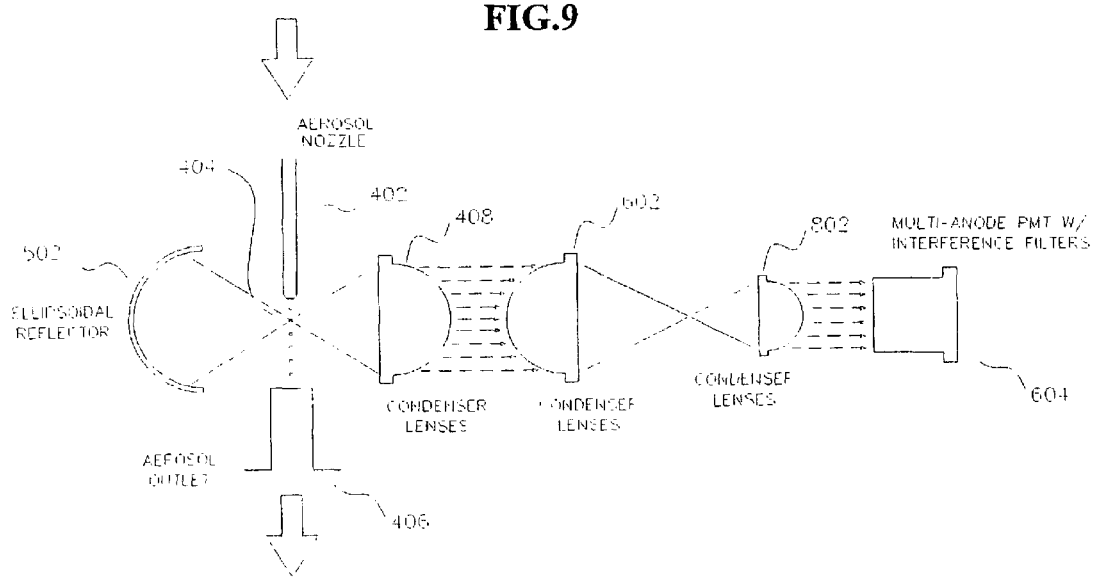
FIG. 9 is a schematic diagram illustrating another embodiment of the detection optics of the present invention.

FIG. 9 is schematic diagram illustrating another embodiment of the detection optics of the present invention. An ellipsoidal reflector 502 is used to reflect light that travels away from multi-anode PMT 604 back to multi-anode PMT 604 rather than condenser lens 414 and mirror 416 as shown in FIG. 8.

Figure 10:
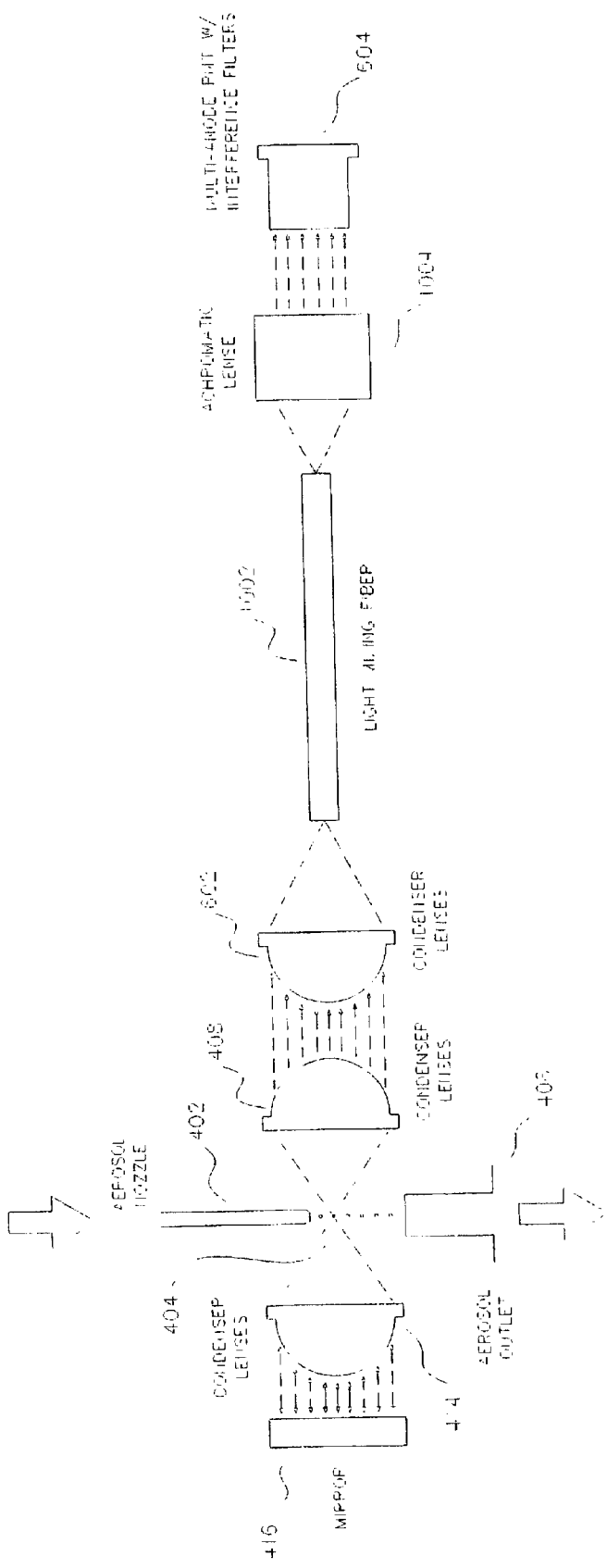
FIG. 10 is a schematic diagram illustrating another embodiment of the detection optics of the present invention.

FIG. 10 is a schematic diagram illustrating another embodiment of the detection optics of the present invention. In the embodiment shown in FIG. 10, a focusing element such as condenser lens 602 focuses the light emanating from view volume 404 into a light mixing fiber 1002. Light mixing fiber 1002 removes errors that may be introduced as a result of the positioning of the aerosol particle when it is illuminated. For example, light mixing fiber 1002 can remove inaccuracies due to orientation of the biological particle in the view volume. The output of light mixing fiber 1002 is input to an achromatic lens 1004. Achromatic lens 1004 collimates the light for input into multi-anode PMT 604 so the light can be detected.

Figure 11:
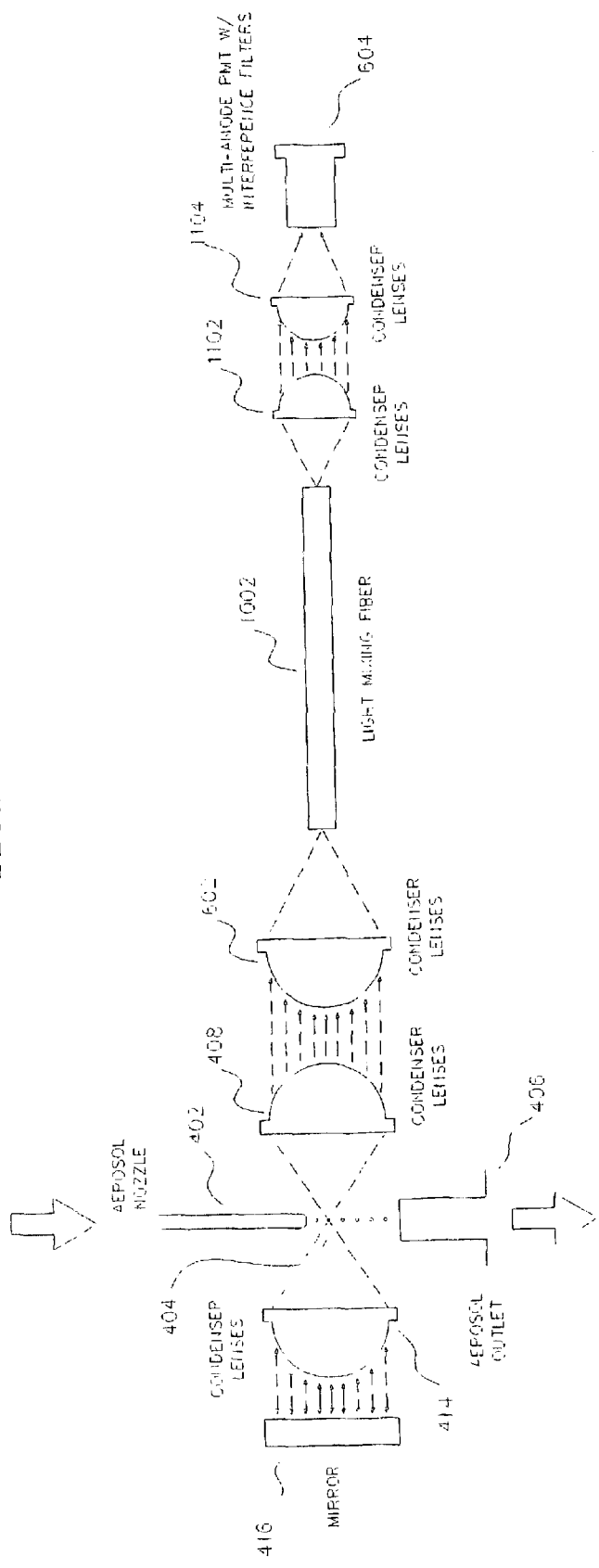
FIG. 11 is a schematic diagram illustrating another embodiment of the detection optics of the present invention.

FIG. 11 is a schematic diagram illustrating another embodiment of the detection optics of the present invention. In FIG. 11, a condenser lens 1102 inputs light output by light mixing fiber 1002. Condenser lens 1102 collimates this light and outputs the collimated light to another condenser lens 1104. Condenser lens 1104 focuses the light onto multi-anode PMT 604. The combination of condenser lenses 1102 and 1104 serves to more precisely focus light exiting light mixing fiber 1002 on multi-anode PMT 604. Preferably, condenser lenses 1102 and 1104 are aspheric condenser lenses. Moreover, preferably, aspheric condenser lenses 1102 and 1104 operate on light from approximately 19 degrees to 140 degrees.

Figure 12:
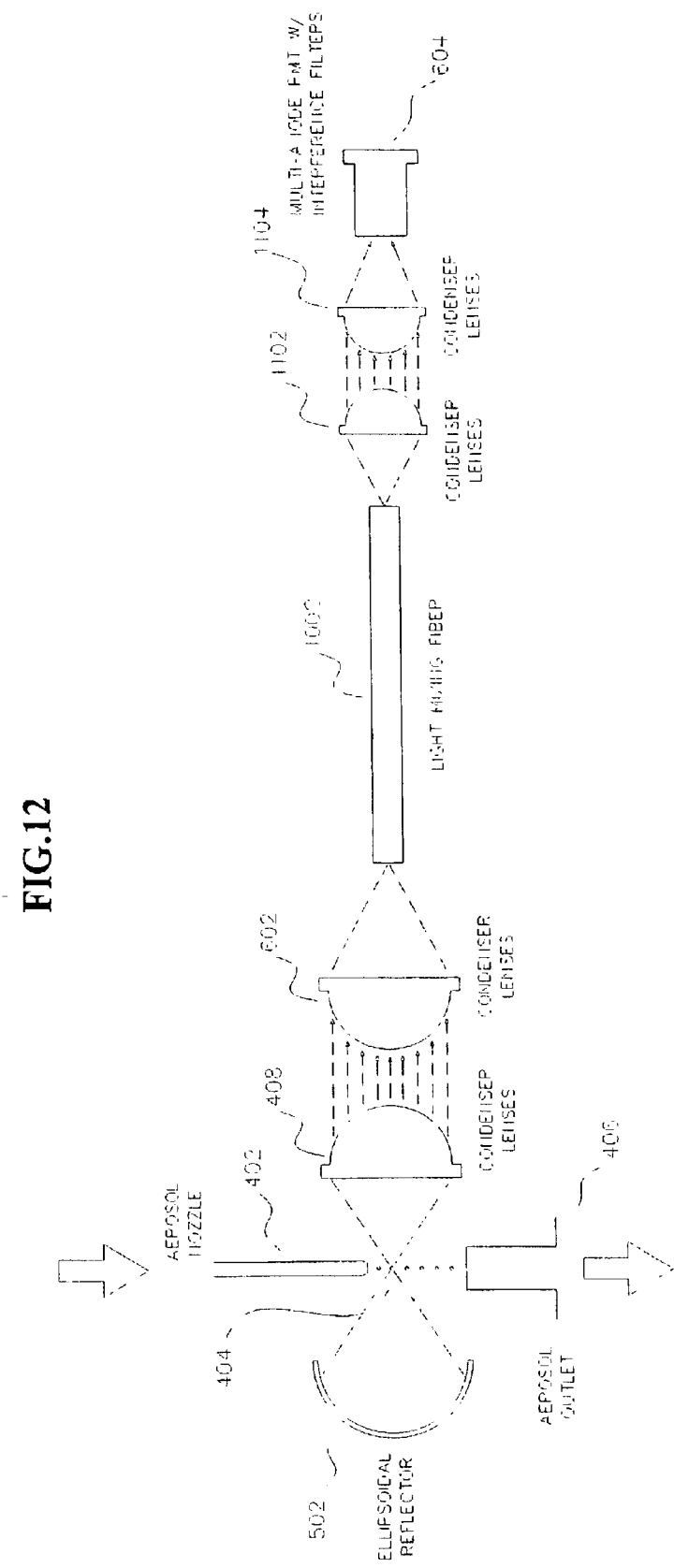
FIG. 12 is a schematic diagram illustrating another embodiment of the detection optics of the present invention.

FIG. 12 is schematic diagram illustrating another embodiment of the detection optics of the present invention. An ellipsoidal reflector 502 is used to reflect light that travels away from multi-anode PMT 604 back to multi-anode PMT 604 rather than condenser lens 414 and mirror 416 as shown in FIG. 10 or FIG. 11.

Additional embodiments of the present invention are also possible. For example, the present invention can be implemented as shown in FIGS. 4, 6, 8, 10 and 11 using only condenser lens 408. In such a configuration, no condenser lens is used to focus light reflecting from mirror 416. Though such a configuration is a sub-optimal solution due to loss of some of the reflected light, it can also be used. Other embodiments of the present invention would be apparent to those having skill in the art from the disclosure provided herein.

Any light detector can be used as a detection device. Three common detectors are (1) PMTs, (2) avalanche photo-diodes; and (3) solid-state silicon photo diodes. Focusing the light may be important depending on the type of detector that is used. For example, avalanche photo-diodes have relatively small detection surfaces. Consequently, when using avalanche photo-diodes, it is preferable to focus the light so as to direct the light to the avalanche photo-diode's detection surface.

In operation, light exits aspheric condenser lens 308 in collimated form. The exiting light reaches a light detector. Preferably, there are a plurality of detectors. Filters are used to pass light of a pre-determined wavelength to a particular detector. Each detector can have a different such filter. In this manner, the present invention can provides multiple channels, each channel capable of processing a different wavelength, simultaneously in real-time. To measure elastic scattering (Mie scattering), a filter that passes only light received having the same wavelength as the light generated by laser source 103 is used. The amount of light detected by the detector to which the light passes is determined and used as the Mie scattering measurement.

Additional collection channels are used to measure intrinsic fluorescence. The additional detection channels each comprise a filter (e.g., a broadband filter or a narrowband interference filter) to pass light corresponding to a fluorescent wavelength of a biological or biochemical component that is desired to be detected. With multiple channels, multiple biological components can be detected.

Preferably, at least two channels are used. Thus, even in the case where only light at a fundamental harmonic of the laser source's laser diode is applied to the particulate aerosol, the interference filter assembly includes at least two filters, one per channel. One of the filters detects light at the fundamental frequency for purposes of the measuring Mie scattering. The filters in the other channels pass light corresponding to a fluorescing wavelength of one or more biological or biochemical components of interest.

Figure 13A:
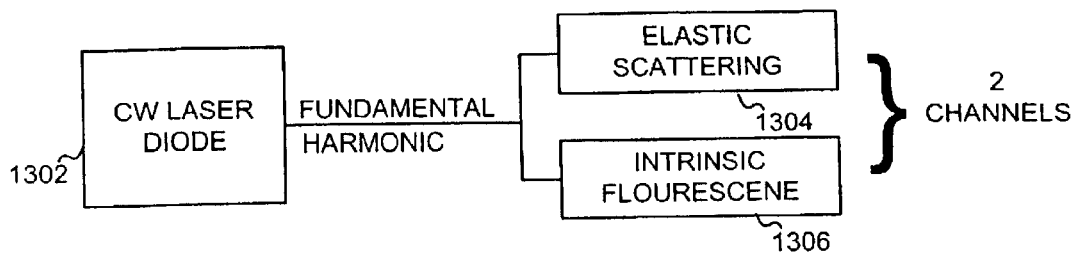
FIG. 13A illustrates a two-channel implementation of the present invention.
Figure 13B:
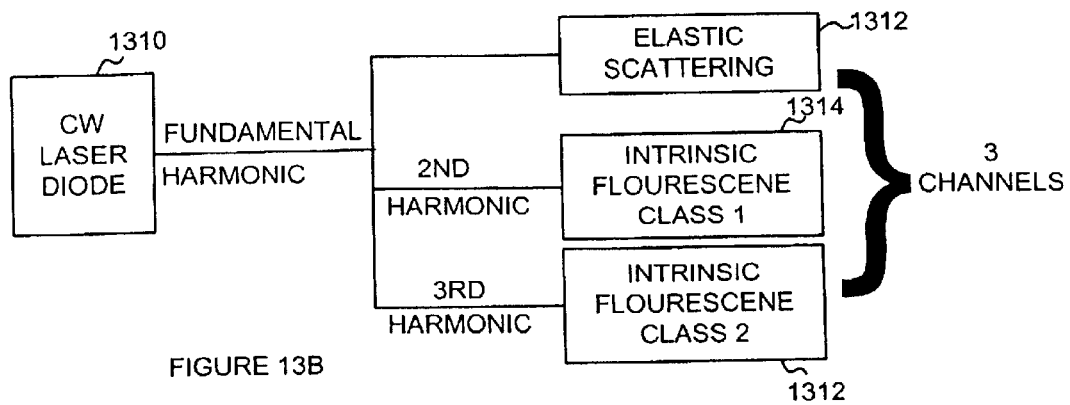
FIG. 13B illustrates a three-channel implementation of the present invention.
Figure 13C:
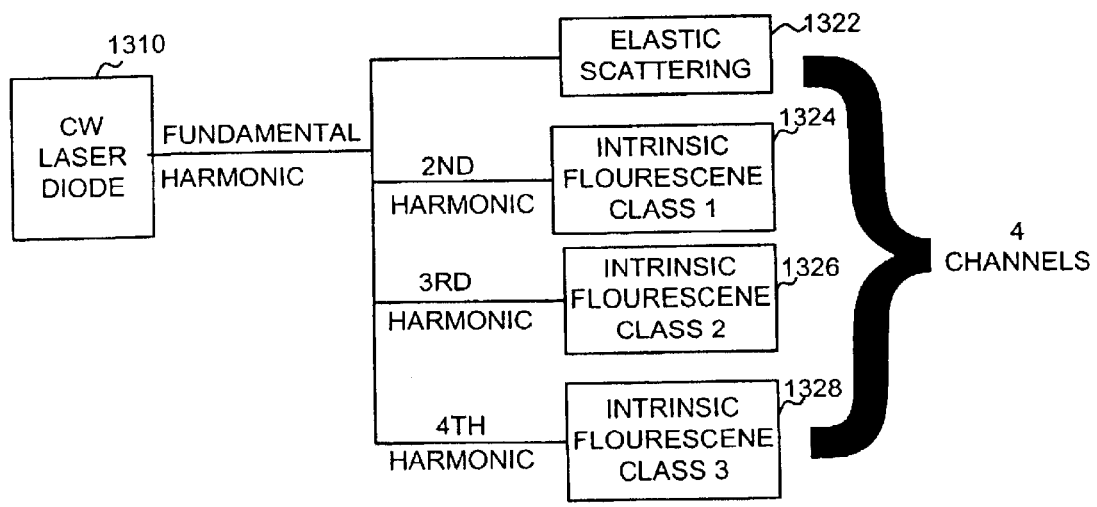
FIG. 13C illustrates a four-channel implementation of the present invention.

FIGS. 13A, 13B and 13C describe the channeling capability of the present invention in more detail. Using channels, the present invention can be measure size and auto-fluorescence from data collected in one or more channels simultaneously, as well as perform ratio-metric. Using this information, the biological particles that are detected can be identified and classified.

FIG. 13A illustrates a two-channel implementation of the present invention. continuous wave (CW) laser 1302 generates a laser beam having a fundamental wavelength. The fundamental wavelength corresponds to a wavelength that causes a biological or biochemical component to fluoresce. For example, CW laser can be a laser diode based laser that generates laser light have a wavelength in the range from approximately 300 nm to 415 nm. For example, one such commercially available laser generates laser light having a wavelength of 405 nm. The 405 nm wavelength can be used for both elastic scattering measurements as well as auto-fluorescence measurements.

Channel 1304 is used for sizing using Mie scattering techniques on the collected light. Channel 1304 preferably includes a filter that substantially passes only light having a wavelength equal to the fundamental wavelength. Channel 1306 measures any auto-fluorescence. Preferably, channel 1306 has a filter that substantially passes only light having a wavelength equal to the fluorescence wavelength for the biological or biochemical component of interest. Ratio-metric calculations can be performed by calculating ratios of peak outputs of channels 1304 and 1306 to one another or by ratios of integrated pulse outputs of channels 1304 and 1306.

FIG. 13B illustrates a three-channel implementation of the present invention. CW laser 1310 generates a laser beam having a fundamental wavelength. The fundamental harmonic in this case does not excite any endogenous fluorophores. Consequently, this harmonic is used only for the elastic scattering measurement. However, the fundamental wavelength is chosen such that harmonics can be generated. The harmonics are associated with wavelengths of fluorescence for biological or biochemical components of interest. As described above, the harmonics can be generated by passing the generated laser beam through a non-linear optical material such as a nonlinear crystal or a glass fiber that has been doped with a nonlinear optical material. Channel 1312 is used for sizing using Mie scattering techniques on the collected light. Channel 1312 preferably includes a filter that substantially passes only light having a wavelength equal to the fundamental wavelength. Channels 1314 measures auto-fluorescence generated by exposing the particles to the second harmonic of the fundamental harmonic. Preferably, channel 1314 includes a filter that substantially passes only light having a wavelength equal to expected auto-fluorescence wavelengths generated by exposing a fluorophore to light having a wavelength of the second harmonic. Channel 1316 measures auto-fluorescence generated by exposing the particles to the third harmonic of the fundamental harmonic. Preferably, channel 1316 includes a filter that substantially passes only light having a wavelength equal to expected auto-fluorescence wavelengths generated by exposing a fluorophore to light having a wavelength of the third harmonic. Ratio-metric calculations can be performed by calculating ratios of peak outputs of channels 1312, 1314 and 1316 to one another.

FIG. 13C illustrates a three-channel implementation of the present invention. CW laser 1320 generates a laser beam having a fundamental wavelength. As with the embodiment shown in FIG. 13B, the fundamental harmonic in this case does not excite any endogenous fluorophores. Consequently, this harmonic is used only for the elastic scattering measurement. However, the fundamental wavelength is chosen such that harmonics can be generated. The harmonics are associated with wavelengths of fluorescence for biological or biochemical components of interest. The harmonics can be generated by passing the generated laser beam through a non-linear optical material such as a nonlinear crystal or a glass fiber that has been doped with a nonlinear optical material. Channel 1322 is used for sizing using Mie scattering techniques on the collected light. Channel 1322 preferably includes a filter that substantially passes only light having a wavelength equal to the fundamental wavelength. Channel 1324 measures auto-fluorescence generated by exposing the particles to the second harmonic of the fundamental harmonic. Preferably, channel 1324 includes a filter that substantially passes only light having a wavelength equal to expected auto-fluorescence wavelengths generated by exposing a fluorophore to light having a wavelength of the second harmonic. Channel 1326 measures auto-fluorescence generated by exposing the particles to the third harmonic of the fundamental harmonic. Preferably, channel 1326 includes a filter that substantially passes only light having a wavelength equal to expected auto-fluorescence wavelengths generated by exposing a fluorophore to light having a wavelength of the third harmonic. Channel 1328 measures auto-fluorescence generated by exposing the particles to the fourth harmonic of the fundamental harmonic. Preferably, channel 1328 includes a filter that substantially passes only light having a wavelength equal to expected auto-fluorescence wavelengths generated by exposing a fluorophore to light having a wavelength of the fourth harmonic. Ratio-metric calculations can be performed by calculating ratios of peak outputs or integrated pulse outputs of channels 1322, 1324, 1326 and 1328 to one another.

Table 3 provides exemplary channel excitation and emission combinations that can be used in particular embodiments of the present invention.

TABLE 3

| Version | Number of Fluorescence, Detection Channels | Fundamental Excitation Wavelength (nm) | Second Harmonic Wavelength (nm) | Third Harmonic Wavelength (nm) | Fourth Harmonic Wavelength (nm) | Emission Wavelengths (nm) | | | |
|---|---|---|---|---|---|---|---|---|---|
| 1 | 1 | 400–405 | | | | 415–690 | | | |
| 2 | 2 | 400–405 | | | | 415–500 | 510–690 | | |
| 3 | 2 | 400–405 | | | | 415–580 | 600–690 | | |
| 2 | 2 to 4 | 808 | 404 | 269 | | 320–350 | 470 | 530 | 580–690 |
| 3 | 2 to 4 | 830 | 415 | 277 | | 320–350 | 470 | 530 | 580–690 |
| 4 | 2 to 4 | 1064 | 532 | 354 | 266 | 320 | 350 | 470 | 580–690 |
| 5 | 2 to 4 | 1047 | 523 | 349 | 261 | 320 | 350 | 470 | 580–690 |
| 6 | 2 to 4 | 1053 | 526 | 351 | 263 | 320 | 350 | 470 | 580–690 |

Figures 14A, 14B:
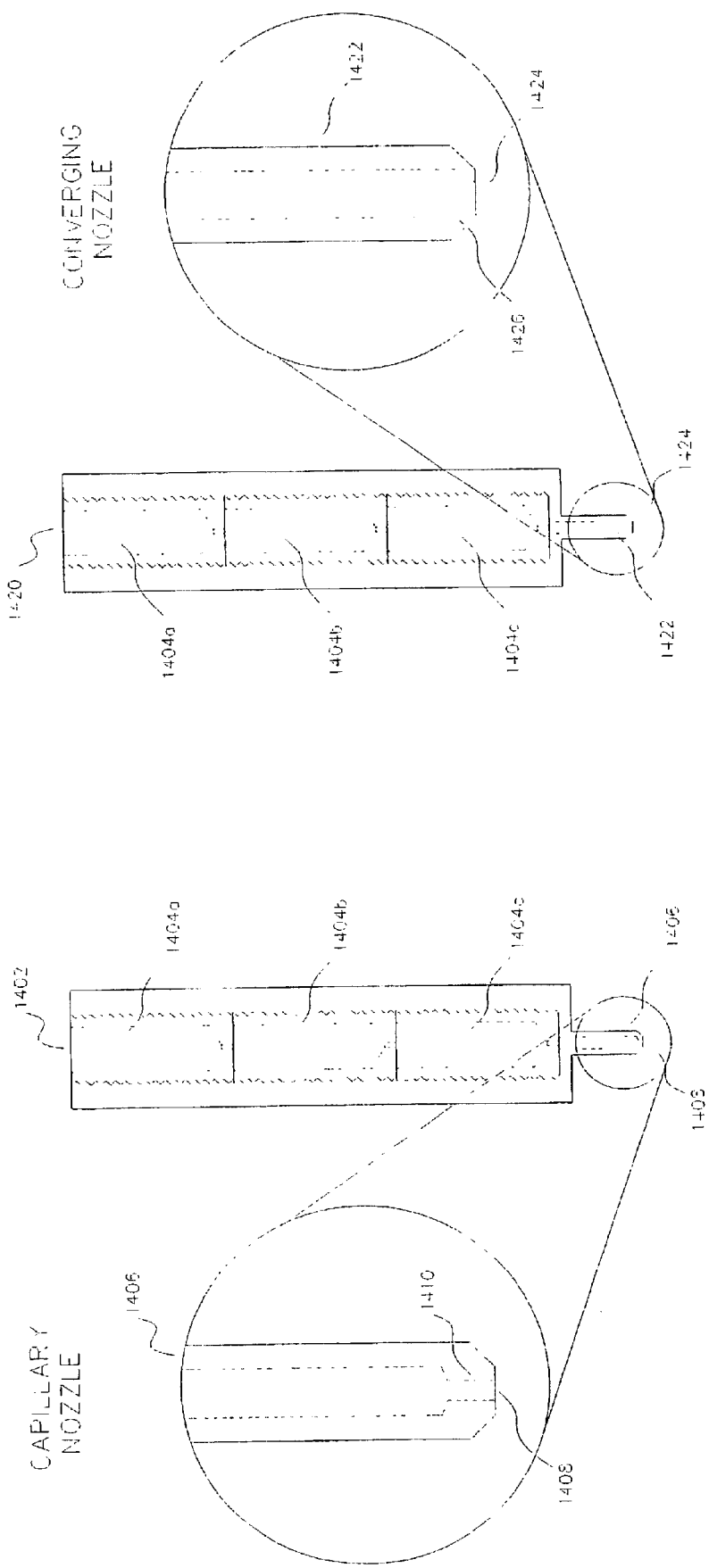
FIG. 14A is a schematic diagram illustrating an aerosol inlet probe according to an embodiment of the present invention.
FIG. 14B is a schematic diagram illustrating an aerosol inlet probe according to another embodiment of the present invention.

FIG. 14A is a schematic diagram illustrating of an aerosol inlet probe 1402 for introducing particles to the laser's view volume according to an embodiment of the present invention. Aerosol inlet probe 1402 comprises one or more aerodynamic pre-focusing elements, for example, pre-focusing elements 1404a, 1404b and 1404c. The pre-focusing elements help to ensure that particles in the aerosol are introduced to the laser's view volume one-at-a-time rather than several at a time. The particles exit aerosol inlet probe one-at-a-time through a primary focusing element. In the embodiment of the aerosol inlet nozzle shown in FIG. 14A, the primary focusing element is a capillary nozzle 1406 (also shown in a detail view). Particles exit capillary nozzle 1006 through an orifice 1408. Preferably, orifice 1408 is $1/39,000^{th}$ of an inch in diameter and an orifice size range of $1/7,000^{th}$ to $1/62,000^{th}$. As shown in the detail view, primary focusing element 1406 includes a capillary nozzle 1410. Capillary nozzle 1410 allows the aerosol to be introduced into the laser's view volume in a collimated form (i.e., in a substantially straight line).

FIG. 14B is a schematic diagram illustrating of an aerosol inlet probe 1420 for introducing particles to the laser's view volume according to another embodiment of the present invention. Aerosol inlet probe 1420 comprises one or more aerodynamic pre-focusing elements, for example, pre-focusing elements 1404a, 1404b and 1404c. The pre-focusing elements help to ensure that particles in the aerosol are introduced to the laser's view volume one-at-a-time rather than several at a time. The particles exit aerosol inlet probe one-at-a-time through a primary focusing element. In the embodiment of the aerosol inlet nozzle shown in FIG. 14B, the primary focusing element is a converging nozzle 1422 (also shown in a detail view). Particles exit converging nozzle 1422 through an orifice 1424. Preferably, orifice 1424 is $1/39,000^{th}$ of an inch in diameter and an orifice size range of $1/7,000^{th}$ to $1/62,000^{th}$. As shown in the detail view, primary focusing element 1422 includes a converging nozzle 1426. Converging nozzle 1426 allows focusing of the aerosol in a converging manner into the laser's view volume.

Pre-focusing elements 1404a, 1404b and 1404c are a series of small orifices used to focus the aerosol into a center air stream prior to introducing it into the primary focusing element. Preferably, each pre-focusing element 1404a, 1404b and 1404c is the same size. As described above, the stages of pre-focusing elements ensure that the particles in the aerosol are positioned in the center of the stream. This is because most of the aerosol stream, i.e., the gas molecules are in the perimeter. The aerosol particles are positioned in the center by each stage of the focusing elements. More stages of pre-focusing elements better positions the particles in the center of the stream to follow a collimated trajectory. In addition, to staging, the diameter of the orifice in each pre-focusing element through which the aerosol is directed to the next stage is restricted because the system is vacuum-driven. For example, in one embodiment of the present invention, the orifice diameter is $1/39,000^{th}$ of an inch and an orifice size range of $1/7,000^{th}$ to $1/62,000^{th}$. Smaller orifices require a higher the pump-loading capacity.

Particle migration through the laser beam is on the order of 50–10000 ns thereby permitting a high particle count rate. A high speed field programmable gate array (FPGA) is used to process the photo-detector signals that are generated as particles pass through the laser's view volume. The FPGA permits real-time analysis of the photo-detector signals collected. The FPGA further includes classifier circuits that perform ratio-metric calculations as described above for comparison of the signals with a library of signatures.

Figure 15:
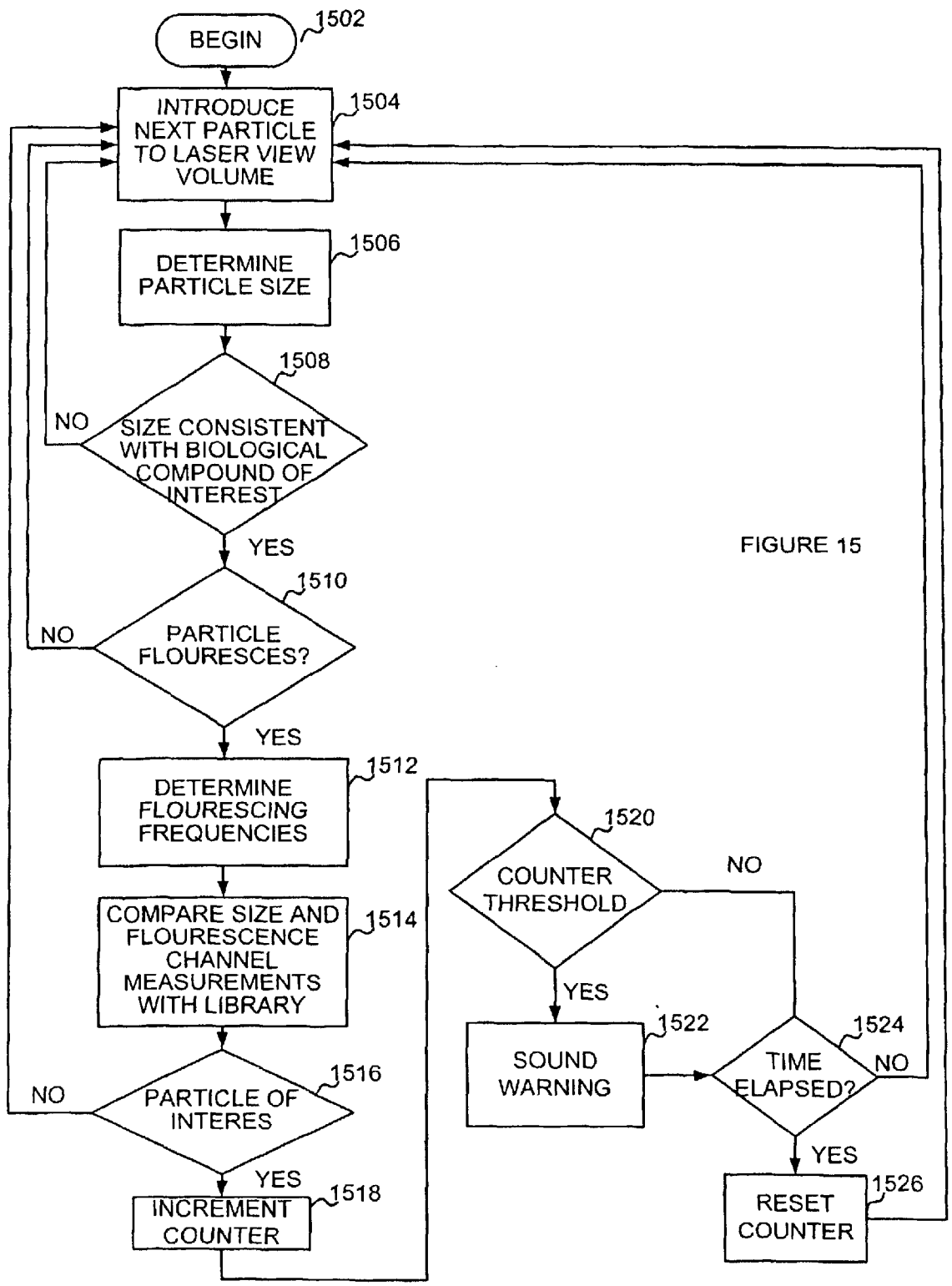
FIG. 15 is a flow chart of a method for providing warning of a detected biological event of interest according to an embodiment of the present invention.

As described above, an exemplary use for the present invention is to provide early warning of a biological event of interest. One such biological event of interest is the introduction of a deadly biological compound such as anthrax to an environment. FIG. 15 is a flow chart for a method for providing warning of a detected biological event of interest according to an embodiment of the present invention. In one embodiment of the present invention, the method illustrated by the flow chart in FIG. 15 is executed on a computer that can be configured to execute the method in conjunction with detection apparatus such as described above. Such a computer will be well-known to those being skilled in the art and need not be described further.

The method begins in step 1502 and immediately continues in-step 1504 with the step of introducing the next particle into the laser view volume. For example, the particles are introduced using an aerosol inlet nozzle (described above). In step 1506, the particle's size is determined. Preferably, the particle's size is determined using Mie scattering techniques. If the size is not consistent with a biological compound of interest, the method continues in step 1504. If the particle's size is consistent with a biological compound of interest, the method continues in step 1510. For example, anthrax has a Mie scattering diameter ranging from approximately 0.8 to 1.4 microns. In a system for detecting anthrax, the method continues to step 1510 if the particle's scattering diameter is determined to fall within the range of 0.8 to 1.4 microns.

In step 1510, it is determined whether the particle fluoresces. Since most, if not all, biological particulates contain fluorophores, if no fluorescence is detected, the particle is either not biological, or does not contain the endogenous fluorophores expected to be observed in the biological compound of interest. In the latter case, although the particle fluoresces, the fluorescence may not be detected if filters are used to pass only light having wavelengths corresponding to those expected to emanate from fluorescing biological components in the biological compound of interest. In step 1512, the method continues with the step of determining fluorescing frequencies.

The method then continues in step 1514 with the step of comparing size and wavelength channel measurements with a library of pre-stored measurement corresponding to the biological compound of interest. For example, ratio-metric calculations can be performed to better classify the particle.

The method continues in step 1518 with the step of determining whether the particle is a biological component of interest. This step is performed by analyzing the results of the comparison of the particle's measurements with the library measurements. The method continues in step 1504 if the particle is not a biological particle of interest.

If the particle is a biological component of interest, in step 1518, a counter is incremented. The counter is a counter that indicates the number of times that the biological component was observed in a period of time. The period of time can be either predetermined or user-adjusted. Multiple counters can be established. Each counter corresponds to a biological compound that is desired to be monitored. In the multiple-counter embodiment of the present invention, the counter corresponding to the biological compound of interest is incremented. The period of time can different for each counter in the multiple-counter embodiment of the present invention.

The method continues in step 1520 with the step of determining whether a counter threshold has been exceeded. The counter threshold corresponds to the number of occurrences of the biological particulate that must be observed in the period of time to give rise to a warning that the biological particulate has been detected. Where multiple biological particulates are monitored, there can be a counter threshold established for each biological particulate.

If the counter threshold is exceeded, the method continues in step 1522 with the step of providing a warning that the biological compound has been observed. After, the warning is provided, the method continues in step 1524 with the step of determining whether the period of time has elapsed. Step 1524 is also performed if the counter threshold was not exceeded. If the period of time has elapsed, the counter corresponding to the biological compound is reset in step 1526. After the counter is reset or if the period of time has not elapsed, the method continues in step 1504.

Figure 16:
FIG. 16 is a schematic diagram of one embodiment of the present invention.

FIG. 16 is a schematic diagram of a system for detecting and classifying a biological particle according to an embodiment of the present invention. A detection apparatus 1602 detects light emitted by Mie scattering or auto-fluorescence as described above. For example, detection apparatus 1602 can include the detection apparatus of any of FIGS. 1–14 above. Preferably, the detected light is converted into one or more electrical signals that are transmitted to a processing 1604. Preferably, processor 1604 is a computer that is configured to process the received signals. For example, as described above, processor 1604 can be a computer that is configured to receive the electrical signals and process them in accordance with the method illustrated in the flow chart of FIG. 15.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for detecting and classifying an airborne biological particle, comprising;
   a single laser to illuminate an individual biological particle wherein the particle is dimensioned to be an inhalable particle;
   a first detector to detect light scattered due to illumination of the airborne biological particle by the laser;
   a second detector to detect fluorescence emission from the airborne biological particle due to illumination of the airborne biological particle by the laser;
   a processor to determine a first peak or integrated pulse amount of light detected by the first detector, a second peak or integrated pulse amount of light detected by the second detector, and to calculate a ratio of the first and second peak or integrated pulse and to compare to a library comprising a plurality of ratios of scattering peaks to auto-fluorescence peaks; and
   wherein the processor compares the calculated ratio with the plurality of ratios stored in the library to classify the airborne biological particle in substantially real-time.

2. The system recited in claim 1, further comprising a third detector to detect light emitted if the airborne biological particle auto-fluoresces at a second auto-fluorescence frequency, and wherein the processor determines a third peak of amount of light detected by the third detector, and calculates a second ratio of the first peak to the third peak, and wherein the processor compares the calculated first and second ratios with the plurality of ratios stored in the library to classify the airborne biological particle.

3. The system recited in claim 2, wherein the processor calculates a third ratio of the second peak to the third peak, and wherein the processor compares the calculated first, second and third ratios with the plurality of ratios stored in the library to classify the airborne biological particle.

4. The system recited in claim 1, further comprising a mirror to reflect light scattered away from the first and second detectors back toward the detectors.

5. The system recited in claim 4 wherein the mirror is an ellipsoidal mirror.

6. The system recited in claim 1, further comprising a photo-multiplier tube assembly in which the first and second detectors are located.

7. The system recited in claim 1, further comprising a multi-anode photo-multiplier tube in which the first and second detectors are located.

8. The system recited in claim 7, further comprising interference filters placed in front of the anodes of the multi-anode photo-multiplier tube, each interference filter passing light of a predetermined frequency.

9. The system recited in claim 1, further comprising a light mixing fiber to transmit the scattered light to the first and second detectors.

10. A method for detecting and classifying an individual airborne biological particle dimensioned to be an inhalable particle, comprising the steps of:

illuminating the airborne biological particle with a laser beam;

detecting, with a first detector, light scattered due to illumination of the airborne biological particle by the laser;

detecting, with a second detector, emitted fluorescence from the biological particle due to illumination of the airborne biological particle by the laser;

determining a first peak amount of light corresponding to the light detected due to scattering;

determining a second peak amount of light corresponding to the light detected due to auto-fluorescence;

calculating a ratio of the first peak to the second peak and;

comparing the calculated ratio with the plurality of ratios stored in a library to classify the airborne biological particle in substantially real-time.

11. The method recited in claim 10, further comprising the steps of:

detecting light emitted if the biological particle auto-fluoresces at a second auto-fluorescence frequency;

determining a third peak of amount of light corresponding to light detected at the second auto-fluorescence frequency;

calculating a second ratio of the first peak to the third peak; and comparing the calculated first and second ratios with the plurality of ratios stored in the library to classify the airborne biological particle.

12. The method recited in claim 11, further comprising the steps of:

calculating a third ratio of the second peak to the third peak; and comparing the calculated first, second and third ratios with the plurality of ratios stored in the library to classify the airborne biological particle.

13. The method recited in claim 10, further comprising the step of reflecting light scattered away from a plurality of light detectors back toward the detectors.

14. The method recited in claim 13, further comprising the step of using an ellipsoidal minor to reflect light scattered away from the light detectors back toward the detectors.

15. The method recited in claim 10, further comprising the step of filtering the light being passed to a plurality of detectors.

16. A system for detecting and classifying an individual airborne biological particle dimensioned to be an inhalable particle, comprising:

means for illuminating the airborne biological particle with a laser beam;

a first means for detecting light scattered due to illumination of the airborne biological particle by the laser;

a second means for detecting emitted fluorescence from the airborne biological particle due to illumination of the biological particle by the laser;

means for determining a first peak amount of light corresponding to the light detected due to scattering;

means for determining a second peak amount of light corresponding to the light detected due to auto-fluorescence;

means for calculating a ratio of the first peak to the second peak and;

means for comparing the calculated ratio with the plurality of ratios stored in a library to classify the airborne biological particle in substantially real-time.

17. The system recited in claim 16, further comprising:

means for detecting light emitted if the airborne biological particle auto-fluoresces at a second auto-fluorescence frequency;

means for determining a third peak of amount of light corresponding to light detected at the second auto-fluorescence frequency;

means for calculating a second ratio of the first peak to the third peak; and means for comparing the calculated first and second ratios with the plurality of ratios stored in the library to classify the airborne biological particle.

18. The system recited in claim 17, further comprising;

means for calculating a third ratio of the second peak to the third peak; and means for comparing the calculated first, second and third ratios with the plurality of ratios stored in the library to classify the airborne biological particle.

19. The system recited in claim 16, further comprising:

means for reflecting light scattered away from a plurality of light detectors back toward the detectors.

20. The system recited in claim 16, further comprising means for filtering the light being passed to a plurality of detectors.

* * * * *